United States Patent [19]
Van Vaals et al.

[11] Patent Number: 5,938,600
[45] Date of Patent: *Aug. 17, 1999

[54] METHOD AND DEVICE FOR HEATING BY MEANS OF ULTRASOUND

[75] Inventors: Johannes J. Van Vaals; Lennart Hofland, both of Eindhoven, Netherlands

[73] Assignee: U.S. Philips Corporation, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/767,596

[22] Filed: Dec. 9, 1996

[30] Foreign Application Priority Data

Dec. 14, 1995 [EP] European Pat. Off. .............. 95203489

[51] Int. Cl.$^6$ ................................................... A61B 5/055
[52] U.S. Cl. ........................ 600/411; 600/419; 324/306; 601/2; 601/3
[58] Field of Search .............................. 128/653.2, 653.3, 128/653.5; 601/2–4; 324/306, 309; 600/411, 419, 410

[56] References Cited

U.S. PATENT DOCUMENTS

| | | | |
|---|---|---|---|
| 5,131,392 | 7/1992 | Jolesz et al. | 128/653.2 |
| 5,178,135 | 1/1993 | Uchiyama et al. | 601/4 |
| 5,307,812 | 5/1994 | Hardy et al. | 128/653.2 |
| 5,590,653 | 1/1997 | Aida et al. | 128/653.2 |

FOREIGN PATENT DOCUMENTS

| | | |
|---|---|---|
| 0558029 | 9/1993 | European Pat. Off. . |
| 0614651 | 9/1994 | European Pat. Off. . |

OTHER PUBLICATIONS

Ehman et al, "Adaptive Technique for High–Definition MR Imaging of Moving Structures", Radiology vol. 173 No. 1, 1989 pp. 255–263.

"On–Line MIR Monitored Noninvasive Ultrasound Surgery" K. Hynynen et al, Proceedings of the Annual International Conference of the IEEE Engineering in Medicine and Biology Society, vol. 14, Paris, France, Oct. 29–Nov. 1, 1992.

Primary Examiner—Ruth S. Smith
Attorney, Agent, or Firm—Dwight H. Renfrew, Jr.

[57] ABSTRACT

A method of heating a target region by ultrasound radiation includes determination of a position of the target region by a magnetic resonance method. The device for carrying out this method includes an ultrasound device and an MR device. By determining movement of the target region utilizing the MR device (100) and an appropriate magnetic resonance method, and by coupling the movement information to the ultrasound device (118) by an electric signal (122, 124), it is achieved that the ultrasound device can be controlled by the movement information. Various possibilities exist for controlling the ultrasound device. According to a first possibility, the focal region is adjusted to be situated within the target region in order to generate ultrasound. Another possibility is to determine from the movement information the instant at which the target region is situated within the focal region of the ultrasound and to generate ultrasound exclusively for a brief subsequent period during which the focal region is still within the target region. Another possibility is to refrain from generating ultrasound when the movement speed is too high. Finally, the movement information can also be used for making the focal region follow the target region during the generation of ultrasound.

21 Claims, 5 Drawing Sheets

METHOD AND DEVICE FOR HEATING BY MEANS OF ULTRASOUND

BACKGROUND OF THE INVENTION

1. Field of the Invention

The invention relates to a method of irradiating a target region by means of ultrasound, a position of the target region being determined by means of a magnetic resonance method. The invention also relates to a device for carrying out such a method.

2. Description of the Related Art

A method of this kind is known from U.S. Pat. No. 5,307,812. The known method is used to heat the target region of an object, for example within the body of a patient, by means of ultrasound. To this end, an MR image is formed wherefrom an operator derives the position of the target region. Subsequently, the focal region of the ultrasound to be generated is adjusted so as to be situated within the target region. After activation of the ultrasound source, the target region is heated by the ultrasound generated. In order to monitor the heating process, subsequently a temperature-position profile of the target region is determined by means of magnetic resonance. An operator derives the position of the focal region from the temperature-position profile. The operator can subsequently readjust the position of the focal region. An application of this known method can be found, for example in the field of cancer therapy in which a tumor within the body of the patient is heated, thus destroying the tumor cells.

It is a drawback of the known method that, when the target region of the body moves, for example due to the patient's respiration, body tissue which does not belong to the target region is moved into the focal region, so that it is undesirably heated by the ultrasound.

SUMMARY OF THE INVENTION

It is inter alia an object of the invention to provide a method which ensures that heating by the ultrasound is concentrated within the moving target region. To this end, the method in accordance with the invention is characterized in that movement of the target region is determined by means of an appropriate magnetic resonance method. According to this step a processing unit determines the movement or the instantaneous position of the target region from the MR signals received. This information is subsequently used to control the ultrasound source. It is thus achieved that the heating by means of the ultrasound is concentrated substantially exclusively within the moving target region and that tissue outside the target region is hardly heated.

A version of the method in accordance with the invention is characterized in that the irradiation of the target region by the ultrasound is performed by adjusting a focal region of the ultrasound to be generated to a position within the target region by means of position and/or movement information obtained by means of the MR method, and by generating at least one ultrasound pulse, these steps being repeated for a period of time. It is thus ensured that the focal region stays within the moving target region for a prolonged period of time, the heating thus being concentrated therein. It is a further advantage that the focal region of the ultrasound to be generated can thus be moved to successive positions within the moving target region, so that the moving target region can be substantially uniformly heated.

This version of the method in accordance with the invention is also characterized in that the following steps are executed during the generating of the ultrasound pulse:

determining the position within the target region by means of the MR method, and adjusting the focal region of the ultrasound to be generated to the position thus determined within the target region.

The readjustment of the focal region during the ultrasound pulse, being continuously repeated during the ultrasound pulse, ensures that the target region is not displaced to such an extent that the focal region is no longer within the target region.

A further version of the method in accordance with the invention is characterized in that irradiation of the target region by the ultrasound takes place by adjusting a focal region of the ultrasound to be generated to a position, determining a period of time during which the focal region is situated within the target region by means of the MR method, and generating at least one ultrasound pulse during the period of time determined. As a result of the generating of one or several ultrasound pulses during the period of time in which the adjusted focal region is within the moving target region, or is coincident therewith, a volume within the moving target region is heated. The tissue outside the target region, therefore, is not or only hardly heated by the ultrasound, and hence is not damaged. Generally speaking, the position of the focal region to be chosen is situated within the body of a patient, but it may also be temporarily situated just outside the body.

The method in accordance with the invention is also characterized in that movement of the target region is determined by performing the following steps:

a. generating and receiving an MR navigator signal in the body, b. determining a position of the target region from the MR navigator signal received.

The position of a moving region can be determined by generating the MR navigator signal in the body and receiving it. This moving region may be the moving target region itself or another region of the body whose position is unambiguously linked to that of the moving target region. The region in which the MR navigator signal is generated contains, for example the target region which moves in a first direction and an adjacent region of the body. The MR navigator signal has only a frequency code and is generated independently of other spatially encoded MR signals. The frequency code is applied, during the reception of the MR navigator signal, by means of a magnetic gradient field whose gradient direction corresponds to the direction in which the movement component is measured, preferably the movement direction of the target region or the other region.

A one-dimensional MR navigator signal is generated, for example in a cylindrical region whose longitudinal axis extends parallel to a movement direction and which contains the target region of the moving part. Subsequently, a one-dimensional proton density profile of the region in the first direction is derived from the MR navigator signal received, for example by means of one-dimensional Fourier transformation. The position of the target region is determined from the proton density profile by means of the processing unit. A difference with respect to the method disclosed in the cited U.S. Pat. No. 5,307,812 consists in that according to the known method MR signals are generated which are sensitive to temperature variations and wherefrom a temperature-position profile is derived. A further difference consists in that an operator determines the position of the focal region within the body from the temperature-position profile instead of being obtained automatically.

The method of the invention is also characterized in that the following steps are performed in order to determine movement of the target region:

a. generating and receiving a flow-corrected MR navigator signal,
b. generating and receiving an MR navigator signal which is not flow-sensitive,
c. determining a speed of a moving region from the MR navigator signal received.

Thus, the speed is determined of the target region or of another region of the body whose speed is unambiguously linked to that of the target region. The measured speed can be used for controlling the ultrasound unit in various ways. A first way consists in that, when the speed is found to exceed a threshold value so that the heating of the target region by the ultrasound to a value beyond a desired temperature becomes uncertain, the generating of the ultrasound can be postponed until the speed of the target region has dropped below the threshold value. Another way consists in that the speed of the target region determined is used to estimate the position of the target region after a given adjusting period, the estimated position of the target region after the adjusting period being adjusted as the position for the focal region. The adjusting period is, for example the response time of an ultrasound device for adjustment of the focal region of the ultrasound to a variation of the position signal.

The method in accordance with the invention is also characterized in that movement of the target region is determined by reconstructing an MR image by means of a fast MR imaging pulse sequence and by subsequently determining a position of a moving region from the MR image. The movement of the target region can also be determined by applying a fast MR imaging pulse sequence. The moving region reproduced in the MR image can represent the target region itself or another region whose position is unambiguously linked to that of the target region. On the basis of the movement thus determined, the heating can be controlled in a manner analogous to the method described above. In the context of the present invention a fast MR imaging pulse sequence is to be understood to mean an MR imaging pulse sequence producing an image of the moving target region, including reconstruction, within a period of time which is substantially shorter than the displacement time of the target region in the field of vision of the MR image. Such a fast imaging pulse sequence is, for example a GRadient and Spin Echo (GRASE) method, an Echo Planar Imaging method, or a projection-reconstruction method, followed by the reconstruction of an MR image from the MR signals received.

The invention also relates to a device for irradiating a target region by means of ultrasound, including an MR device, characterized in that the control unit is also arranged to determine, from the MR signals processed, a position of a target region within the body in order to control the ultrasound source in response to the position determined. The ultrasound source can be controlled directly by deriving a position from the data of the MR signals received, for example a proton density profile or a reconstructed image.

An embodiment of the device in accordance with the invention is also characterized in that the control unit generates a position signal representing the position determined, that the ultrasound unit includes a position control input, and that the focal region of the ultrasound to be generated is dependent on the position signal presented to the position control input. As a result of this step, the position determined for the moving target region is applied directly to the ultrasound source so that the adjustment of the focal region can be carried out. The voltage of the position signal generated represents, for example the instantaneous position of the moving target region relative to the ultrasound source.

A further embodiment of the device in accordance with the invention is also characterized in that the control unit generates a trigger signal in dependence on the position determined, and that the ultrasound unit is arranged to generate ultrasound upon presentation of the trigger signal. This step determines the period of time during which the focal region is present within the target region. The target region is heated by the ultrasound during this period of time.

These and other aspects of the invention will be apparent from and elucidated with reference to the embodiments described hereinafter.

DETAILED DESCRIPTION OF THE PREFERRED EMBODIMENTS

Figure 1:
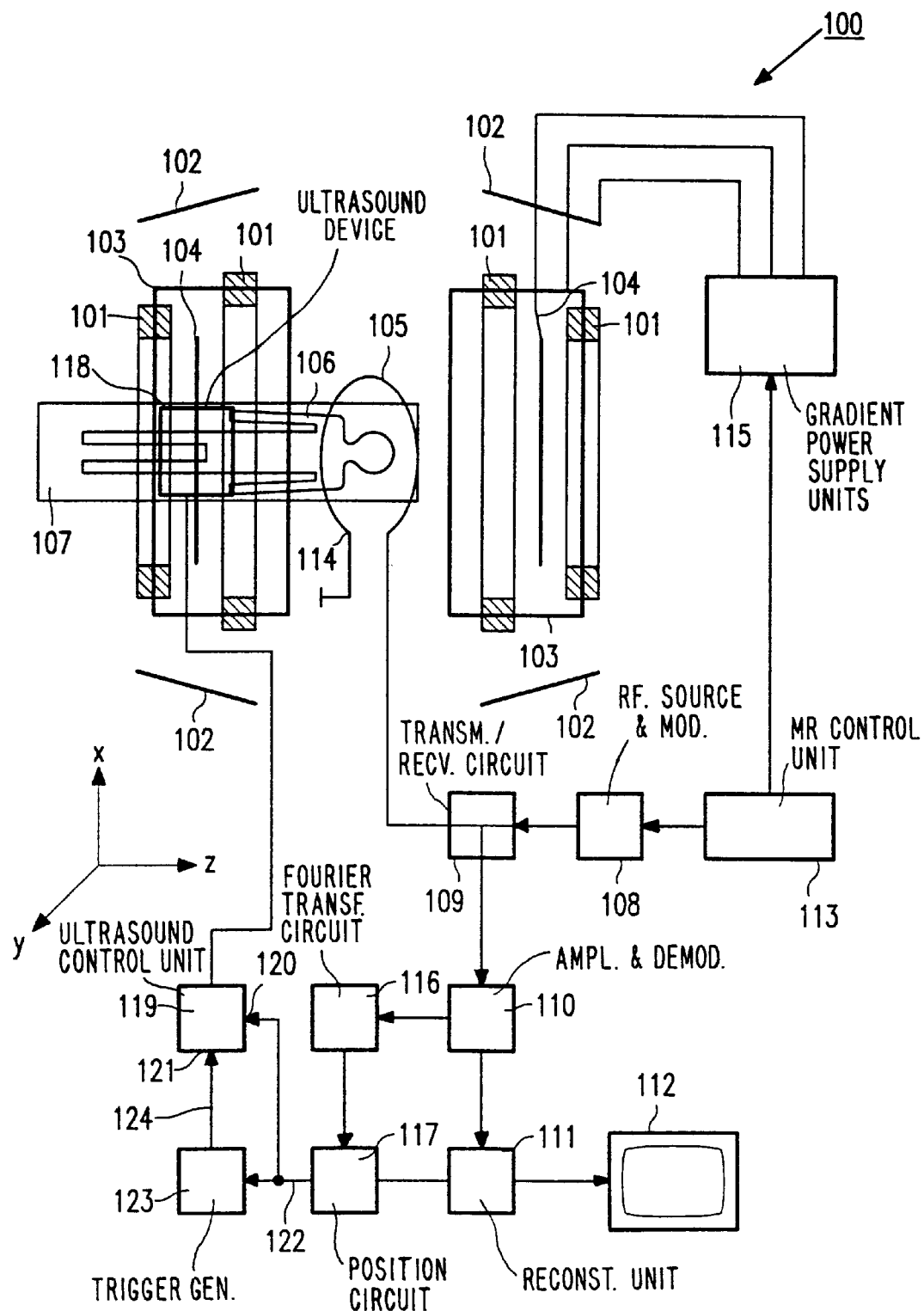
FIG. 1 shows a device which includes an MR device and an ultrasound device.

FIG. 1 illustrates a device 100 in accordance with the invention. The device includes a magnetic resonance device and an ultrasound device. The MR device includes a first magnet system 101 for generating a static magnetic field, a second magnet system 102, 103, 104 for generating temporary magnetic gradient fields in three orthogonal directions, and power supply units 115 for the second magnet system 102, 103, 104. The power supply for the first magnet system 101 is not shown. The device also has an examination space which is large enough to accommodate a part of a body 106 to be examined or treated which is possibly arranged on a support 107. As is customary, the z-direction of the coordinate system shown in this figure indicates the direction of the static magnetic field. Furthermore, the MR device includes an RF transmitter coil 105 which serves to generate RF fields and is connected to an RF source and modulator 108. The RF transmitter coil 105 is arranged around or near a part of the body in the examination space. The MR device includes a receiver coil 114 for receiving a magnetic resonance signal. This coil may be a separate coil or the same coil as the RF transmitter coil 105. The RF transmitter/receiver coil 105 is connected to a signal amplifier and demodulation unit 110 via a transmission/receiving circuit 109. A sampled phase and a sampled amplitude are derived from the MR signals received in the signal amplifier and demodulation unit 110. Subsequently, the sampled phase and sampled amplitude are applied to a reconstruction unit 111. The reconstruction unit 111 processes the applied phase and amplitude by way of, for example a two-dimensional Fourier transformation so as to form an image. This image is displayed by means of a monitor 112. The magnetic resonance device 100 also includes an MR control unit 113. The MR control unit 113 generates control signals for the RF transmitter 108, the power supply units 115 and the reconstruction unit 111. It is to be noted that for the present invention the details of the MR device are not of essential importance. The invention can also be used in conjunction with a type of MR device other than that shown in FIG. 1.

The device in accordance with the invention also includes an ultrasound device 118 for generating ultrasound. The ultrasound device 118 includes a number of ultrasound transducers and an ultrasound control unit 119. The circular ultrasound transducers are mounted, for example concentrically on the support 107 in the plane of the support 107 of the MR device. The ultrasound transducers convert an electric control signal presented by the ultrasound control unit 119 into ultrasound. The ultrasound control unit 119 also includes inter alia a position signal input 120 and/or a trigger input 121. When the ultrasound control unit 119 includes a position signal input 120, the control unit 119 of the ultrasound device 118 determines the amplitude and the phase of each of the control signals from the value of the position signal 122 on the position input 120. The control signals control the ultrasound transducers. As a result, the focal region can be very quickly adjusted, for example in less than 10 ms, to a position along a line parallel to the Y-axis of the coordinate system shown, substantially perpendicularly to the plane of the ultrasound transducers.

If the control unit 119 includes, additionally or instead of the position signal input 120, a trigger input 121 for a trigger signal 124 generated by a trigger generator 123 in dependence on the position determined by position circuit 117, the control unit 119 generates an adjustable number of ultrasound pulses during an adjustable period of time when the trigger signal 124 is activated on the trigger input 121. The number of ultrasound pulses, or the duration of the ultrasound pulses, can be adjusted by an operator.

The device in accordance with the invention also includes a Fourier transformation circuit 116 for performing a 1D Fourier transformation, and a position circuit 117 for determining a position from the result of the Fourier transformation circuit 116 and for generating a position signal 122. The position circuit 117 may also be arranged to determine a position from a reconstructed image from the reconstruction unit 111.

With a view to generating MR signals so as to obtain an image of the target region within the body, preferably a known imaging pulse sequence is used, for example a gradient echo imaging pulse sequence. This sequence will be described with reference to FIG. 2.

Figure 2:
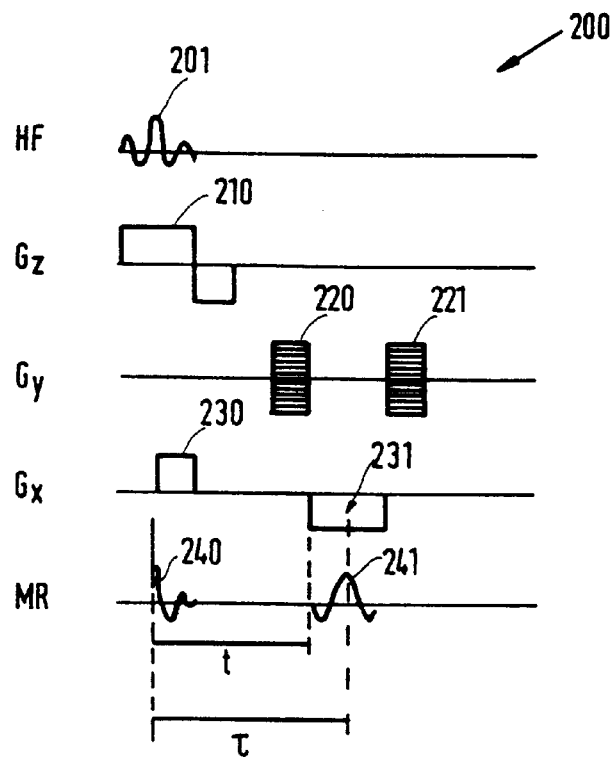
FIG. 2 shows an imaging pulse sequence.

FIG. 2 shows an example of a known imaging pulse sequence 200 which is used to generate MR signals 240, 241 in an object or body in order to reconstruct an image therefrom, for example by means of a two-dimensional Fourier imaging technique. The pulse sequence 200 commences with an excitation pulse 201 having a flip angle α. The flip angle α is, for example 90°. The pulse 201 selectively excites a slice of the body upon application of a first temporary magnetic gradient field 210 whose gradient direction corresponds to the z-direction. The excitation pulse 201 generates a first magnetic resonance signal 240. The first magnetic resonance signal 240 quickly decays due to the dephasing of the individual nuclear spins caused by an applied second temporary magnetic gradient field 230 having a gradient direction corresponding to the x-direction. After a period t in FIG. 2 a third temporary magnetic gradient field 231 is applied whose gradient direction opposes the direction of the second temporary magnetic gradient field 230. The dephasing is thus converted into rephasing so that after a period $T_1$ a second MR signal 241 arises. The phase encoding of the second MR signal 241 is determined by a fourth temporary magnetic gradient field 220, having a gradient direction corresponding to the Y-direction. Spatial encoding in the MR signals of the entire slice can be achieved by increasing the strength of the temporary magnetic gradient field $G_y$, applied in the interval between the temporary gradient fields 230, 231, in successive pulse sequences, for example from a minimum value to a maximum value in 256 steps. The dephasing effect of the fourth temporary magnetic gradient fields 220 is canceled by application of a fifth temporary magnetic field 221 after the appearance of the second MR signal 241, its gradient direction opposing that of the previously applied fourth temporary magnetic gradient fields 220. The frequency encoding of the second MR signal 241 is realized by the third temporary magnetic gradient field 231. After, for example 256 MR signals have been generated by repeated application of the pulse sequence 200, an image of the moving part is determined from the received and sampled MR signals by execution of, for example a two-dimensional Fourier transformation in the reconstruction unit 111. The image is subsequently displayed on the monitor 112.

In the image a target region in the body is indicated so as to be heated by means of the ultrasound to be generated. The position of the target region is subsequently applied to the ultrasound device 119. The target region is, for example a region of carcinomatous tissue having a cross-section of approximately 2 cm in the liver of the body 106 of a patient. The focal region of the ultrasound is, for example a cylinder having a diameter of 2 mm and a length of 10 mm.

In order to heat the tissue of the target region, the target region is scanned by the focal region under the control of the ultrasound device, only the tissue present within the focal region being heated beyond a given selectable limit temperature. The temperature of the heated spot can be measured by means of MR. The problem encountered during heating is that, for example the liver carcinoma moves due to respiration, and hence is not heated, whereas due to this movement other, non-carcinomatous tissue enters the focal region so that it is heated. When information concerning the movement of the target region is determined, the ultrasound device can be controlled directly by this information so as to avoid heating of undesirable regions.

In order to determine the movement of the target region in a body of a patient, in a first embodiment of the invention MR navigator signals are generated. For example, it is assumed that the target region moves in a first direction, parallel to the Y-axis of the coordinate system shown in FIG. 1. With a view to generating MR navigator signals, for example a region which contains the target region and surrounding tissue of the body is excited by means of RF signals. It is alternatively possible to select instead of the target region another moving region in the body whose position and speed are unambiguously linked to those of the target region. This may be, for example, the diaphragm of the body 106 of a patient whose position and speed are substantially unambiguously linked to the position and the speed of the liver of the patient. The advantage thereof consists in that the diaphragm is imaged with a suitable contrast in an MR image, thus enabling suitable position measurement. The generating of the MR navigator signals will be described with reference to FIG. 3.

Figure 3:
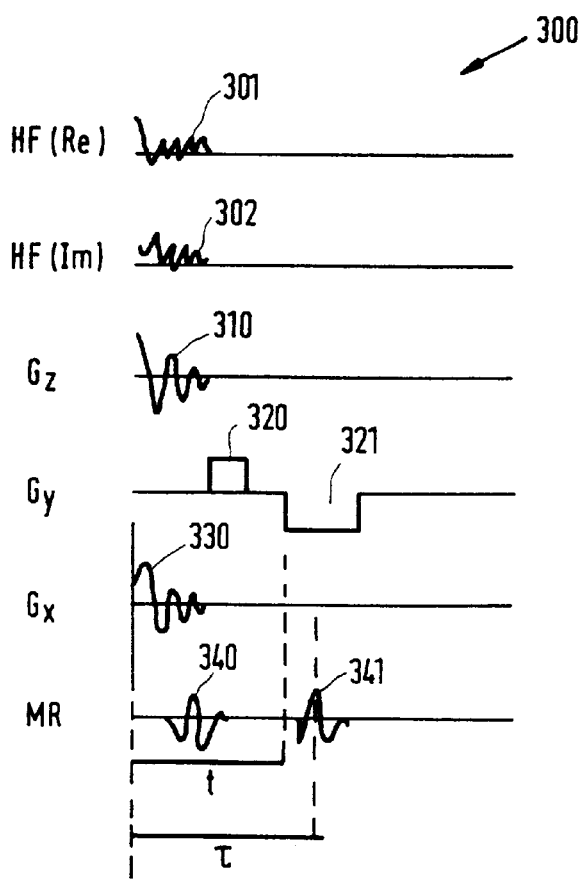
FIG. 3 shows a pulse sequence for generating an MR navigator signal.

FIG. 3 shows an example of a pulse sequence 300 for generating an MR navigator signal 341. An RF pulse 301, 302 is generated in combination with a suitably chosen sixth temporary magnetic gradient field 310 whose gradient extends in the x-direction and a suitably chosen seventh temporary magnetic gradient field 330 whose gradient direction extends in the z-direction. The cylinder is thus excited. In order to determine a movement in an arbitrary direction, the direction of the major axis of the cylinder can be adapted by suitably chosen temporary magnetic gradient fields having gradient directions in the X, Y and Z directions. The RF pulse 301, 302 furthermore has a real part 301 and an imaginary part 302, or in other words a given amplitude and phase. The determination of the real part 301 and the imaginary part 302 of the RF pulse and of the strength and direction of the temporary magnetic gradient fields for selective excitation of 1-D or 2-D regions is described in the article "A linear class of Large-Tip-Angle Selective Excitation Pulses", by J. Pauli et al., Journal of Magnetic Resonance, No. 82, pp. 571–587, 1989. The cited article proposes a class of selective excitation pulse sequences utilizing Fourier analysis, the excitation process being considered as the sampling of the applied RF energy of a k-space which is the same as that used for the data acquisition.

The excitation RF pulse 301, 302 generates a first magnetic resonance signal 340. This signal quickly decays due to the dephasing of the individual nuclear spins in a temporary magnetic gradient field 320. After a period t, there is applied a temporary magnetic gradient field 321 whose gradient direction opposes the gradient direction of the previous temporary magnetic gradient field 320. The individual spins are rephased thereby and a second MR signal appears after a period $T_1$, i.e. the MR navigator signal 341. Frequency modulation is achieved by application of the ninth temporary magnetic gradient field 321 during reception of the MR navigator signal 341. After reception of the MR navigator signal 341, it is sampled in, for example 256 points, after which a sampled amplitude and a sampled phase are determined for each point.

In order to determine the movement of the target region, the position is successively determined from the successively sampled MR navigator signals. To this end, a 1D Fourier transformation is performed. A 1D proton density profile of the region is obtained from the 1D Fourier transformation result. The position of the target region along the Y-axis can be determined therefrom, for example by execution of an edge detection algorithm. The edge detection algorithm will be described with reference to FIG. 4.

Figure 4A:
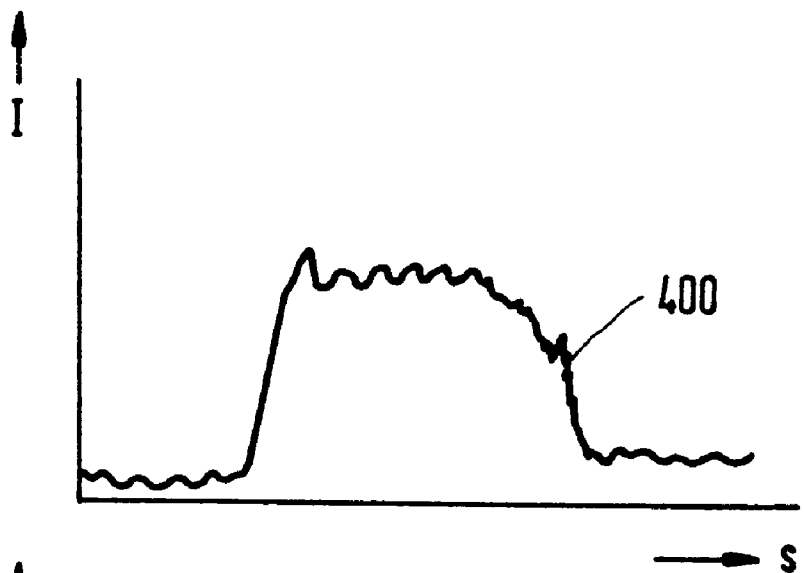
FIG. 4 shows a one-dimensional proton density profile.
Figure 4B:
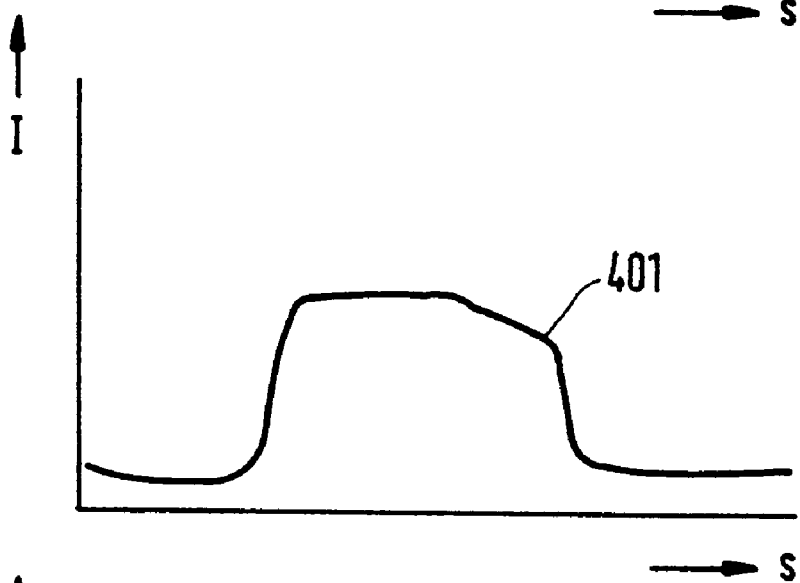
Figure 4C:
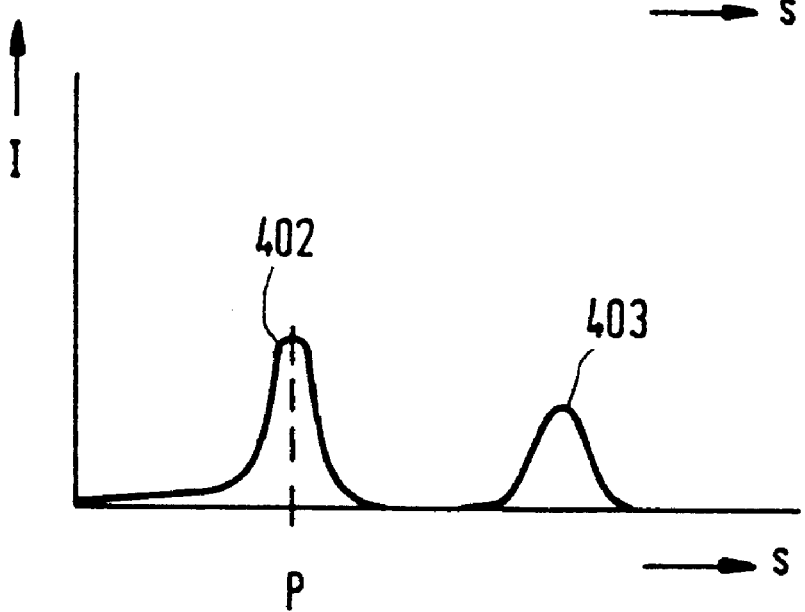

FIG. 4 shows an 1D proton density profile 400. The edge detection algorithm consists of, for example a low-pass filter in series with a high-pass filter. The low-pass filter removes any noise present and produces a filtered 1D proton density profile 401. The high-pass filter determines the edges 402, 403 present from the transitions in the filtered photon density profile 401. The edge 402 represents, for example a transition between the liver and the surrounding tissue. A position for the target region can be derived from the position of the edge 402.

In the device in accordance with the invention, the movement of the target region can be continuously determined and hence the irradiation of the body by ultrasound can be substantially continuously controlled. The speed of determination of the position of the target region, however, must then be sufficiently high. To this end, for example the 1D Fourier transformation is executed in a separate fast Fourier transformation circuit 116 and the digital filtering operations and the determination of the position of the target region are carried out in a separate position circuit 117. These circuits may be special-purpose digital circuits or commercially available programmable digital processing units storing programs for executing the 1D Fourier transformation, the digital filtering and the determination of the position of the target region.

In another embodiment of the invention the ultrasound is controlled by continuously adjusting the focal region within the target region; in another embodiment this is realized by determining a period of time in which the focal region is within the target region, ultrasound being generated exclusively during this period of time.

In a device in which the focal region of the ultrasound to be generated is adjusted to a target region along a line parallel to the Y-axis, the measured position of the target region is converted into a position signal 122 which is applied to the position signal input 120 of the control unit 119 of the ultrasound device 118. The adjustment of the focal region will be described in detail with reference to FIG. 5.

Figure 5:
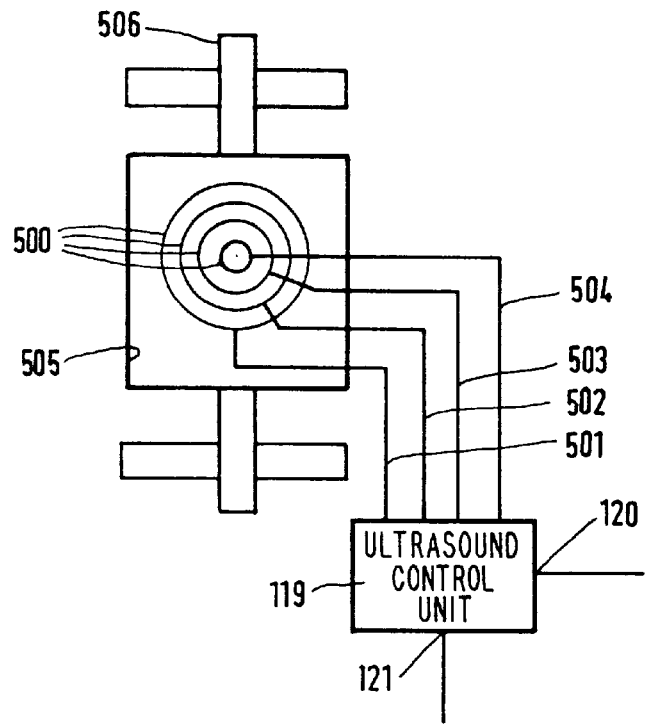
FIG. 5 shows an ultrasound source with a control unit.

FIG. 5 shows the ultrasound device 118 which includes a number of, for example four circular, concentric ultrasound transducers 500. The ultrasound transducers are concentrically mounted on a support 505. The control unit 119 subsequently adjusts the focal region of the ultrasound to be generated to the position along the Y-axis in conformity with the value of the position signal 122 present on the position signal input 120. To this end, the control unit 119 generates four control signals 501, 502, 503 and 504 for the ultrasound transducers 500 and for each ultrasound transducer 500 the phase and amplitude of each control signal 501, 502, 503 and 504 are adjusted to the transit time of the ultrasound wave between the ultrasound transducer 500 associated with a control signal and the position S of the focal region to be adjusted, so that the interference of the composite wave front of the generated waves is maximum in the focal region to be adjusted. The frequency of the ultrasound used has a fixed value of between, for example 1 and 1.5 MHz. The applied acoustic power is, for example 500 W. The focal region of the ultrasound in the tissue corresponds to, for example a cylindrical region having a diameter of, for example 2 mm and a length of, for example 10 mm. If the ultrasound transducers 500 are mounted on a mechanical positioning device 506 which is built, for example into the support 107 of the MR device, adjustment of the focal region of the ultrasound is also possible in the X, Z plane. If no concentric ultrasound transducers are used, but instead the ultrasound transducers 500 are regularly arranged, for example in a matrix, parallel to the support 107, the position of the focal region can be adjusted in a three-dimensional space above the support. Various feasible configurations for arranging the ultrasound transducer on the support will be described with reference to FIG. 6.

Figure 6:
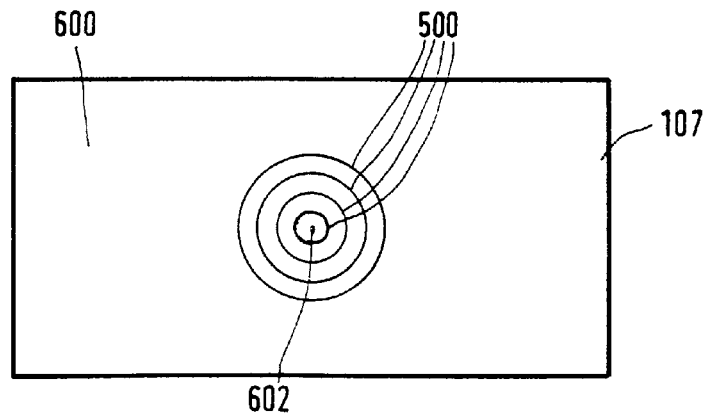
FIG. 6 shows two configurations for the ultrasound transducers.
Figure 6:
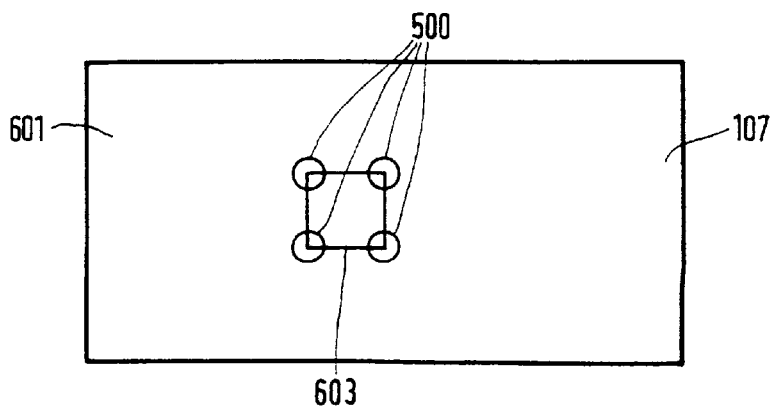

FIG. 6 shows a first configuration 601 of four concentric ultrasound transducers 500, arranged concentrically with respect to the center 602 in a support 107, and a second configuration 601 of four ultrasound transducers 500 arranged, for example in a square 603 in the support 601.

The target region can be actively followed by the focal region of the ultrasound by performing the method in accordance with the invention sufficiently quickly, i.e. generating MR navigator signals, determining the position of the target region from the MR navigator signals, and adjusting the position of the focal region. It is thus achieved that the focal region is always situated within the target region and that heating is concentrated within the moving target region.

Another possibility of using the invention in the device consists in fast, in comparison with the pulse duration of the ultrasound, determination of the position information from the MR navigator signals during irradiation of the target region, and in continuous adjustment of the focal region on the basis thereof. To this end, during an ultrasound pulse, having a pulse duration of, for example 10 seconds, MR navigator signals are continuously generated by means of a pulse sequence 300 in a region which is unambiguously linked to the target region. Using the electronic circuits 116, 117, the position control signal 122 is derived from the received and sampled MR navigator signals. Subsequently, the position of the focal region is continuously readjusted, on the basis of the new position information, by means of the position control signal 122 and the ultrasound control device 119.

A further possibility in accordance with the invention consists in that one or several ultrasound pulses are generated exclusively if a predetermined focal region of the ultrasound is within the target region. This focal region can be adjusted in a target region within the body of a patient, but the focal region can also be adjusted to a position outside the body in such a manner that the focal region is situated only occasionally within the moving region of the body. For example, in the present Application a target region is chosen which is situated within the liver of a patient. Due to, for example movements of the liver parallel to the z-direction as a result of respiration, however, the focal region of the ultrasound to be generated stays within the target region for only a brief period of time. From movement information derived from the MR signals produced there is determined a period of time in which the focal region of the ultrasound device is situated within the target region. To this end, the MR navigator signals are generated within, for example a cylindrical region which contains the target region of the body, the longitudinal axis of the cylinder being chosen so as to extend parallel to the Z-direction. The determination of the movement on the basis of the MR navigator signals received is performed by means of the Fourier transformation circuit 116 and a position circuit 117. The period of time during which the focal region is situated within the target region is determined from the position signal 122 by the trigger circuit 123. When the focal region is situated within the target region, the trigger circuit 123 activates the trigger signal 124. The trigger signal 124 is applied to the trigger input 121 of the control device 119 of the ultrasound device 118. When the trigger signal 124 is active, the control unit 119 of the ultrasound device 118 generates a number of ultrasound pulses which is to be predetermined. Because in accordance with this method ultrasound is generated exclusively during the period of time during which the focal region is situated within the target region, the heating is concentrated within the target region of the moving part.

According to a final possibility offered by the invention, MR images are used to determine the movement of the target region. To this end, MR signals are generated by means of a fast imaging pulse sequence. The reconstruction unit 111 reconstructs MR images from the signals received and sampled. Subsequently, a position of the moving target region is determined from the successive MR images. The speed required for generating a sufficient number of MR signals and for reconstructing an MR image is dependent on the speed of movement of the target region. An example of an MR method which can be used for this purpose is a GRadient and Spin Echo (GRASE) method. The GRASE method is known from U.S. Pat. No. 5,270,654. This fast method enables the formation of several MR images of the moving target region per second. The direction of the plane of the image is chosen in conformity with a direction of movement of the target region by application of suitable temporary magnetic gradient fields. Using the GRASE method, the magnetic resonance device generates and receives MR signals. The processing unit 111 reconstructs MR images from the MR signals received. From each reconstructed MR image a position of the target region can be determined, for example by means of a segmentation technique. Such segmentation can be performed, for example in the position circuit 117 which includes appropriate electronic circuits or software for this purpose. A segmentation technique for determining the position of the target consists, for example in thresholding. After segmentation of the target region, the circuit 117 again derives a position signal 122 from the differences between the positions of the target region.

Generally speaking, for the execution of a segmentation technique there must be sufficient contrast in the one-dimensional proton density profile or the MR image. Such contrast can be enhanced by using various known magnetic resonance contrast enhancement techniques such as inter alia Magnetization Transfer Contrast, selective saturation, inversion and fat suppression. Another possibility of enhancing the contrast is to select, instead of the target region, another moving region offering higher contrast in an MR image. This can be done, for example by selecting a region in the diaphragm of the body of the patient. Another possibility is to administer an MR contrast medium to the patient.

Figure 7:
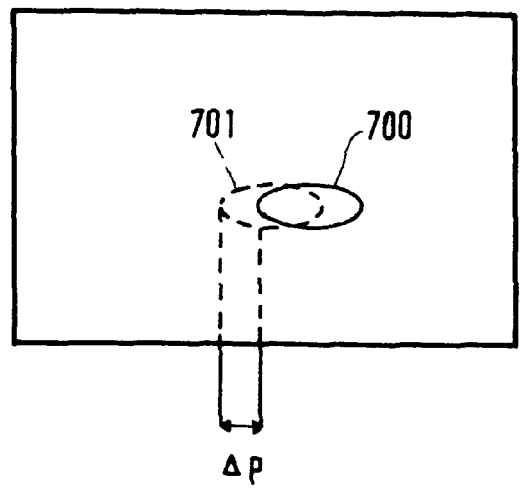
FIG. 7 shows an MR image in which the position of a target region is marked.

In FIG. 7 the result of a thresholding technique is shown in the form of a contour of the target region 700. A position signal 122 is derived from the difference Δp between a first position 700 of the target region of a first image and a second position of the target region 701 of a next MR image. The position signal 122 is subsequently used for controlling the ultrasound. Furthermore, for the determination of movement by means of a magnetic resonance method, it is also possible to measure a speed of the target region or another body region unambiguously linked to the target region. A first method of using the speed determined for control is, for example the determination of a limit speed beyond which no ultrasound is generated. Another way of using the speed determined for controlling the ultrasound is, for example to estimate, on the basis of a given position and a given speed of the target region, a position of the target region after a given period of time, for example the response time of the ultrasound device to a change of the position signal, and to control subsequently the control device of the ultrasound source by means of the estimated position.

In order to determine the speed of the target region, for example two successive MR navigator signals are generated in the target region, the first MR signal being a flow-compensated MR navigator signal whereas the second MR signal is a flow-sensitive MR navigator signal for a flow in a direction to be selected. Generating a flow-compensated MR navigator signal will be described with reference to FIG. 8.

Figure 8:
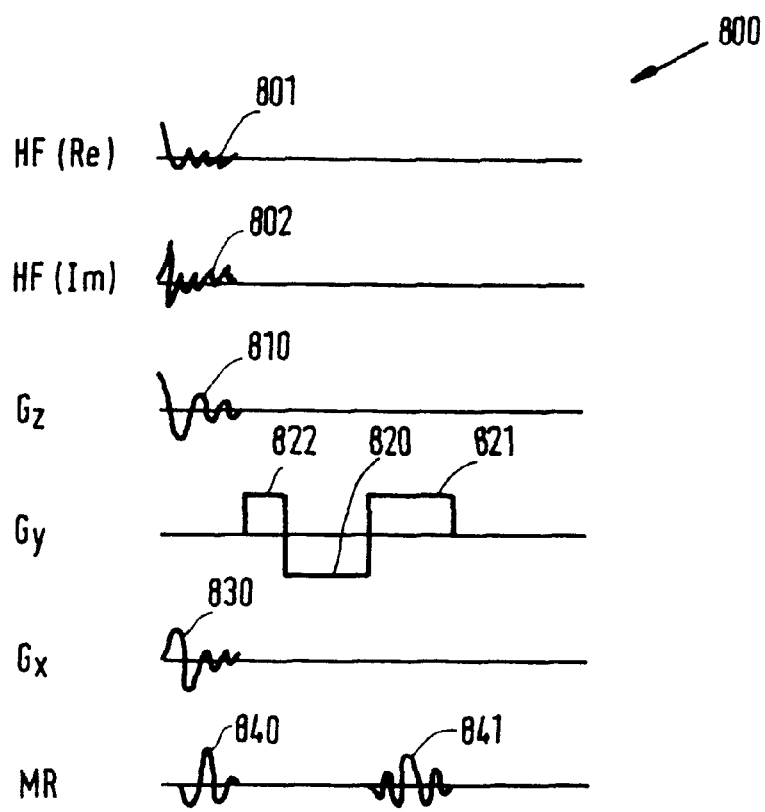
FIG. 8 shows a pulse sequence for generating a flow-compensated MR navigator signal.

FIG. 8 shows a pulse sequence for generating a flow-compensated MR navigator signal 841. The pulse sequence 800 for generating a flow-compensated MR navigator signal is the same as the pulse sequence 300 for generating a flow-sensitive MR navigator signal as shown in FIG. 3, except for the temporary magnetic field 822. This temporary magnetic gradient field provides flow compensation of the MR navigator signal 841. The flow sensitivity of the pulse sequence 300 for generating the MR signal 341 is oriented in the selected gradient direction of the temporary magnetic gradient field 320. In this example the flow direction, i.e. the direction of movement of the target region, is chosen to be oriented in the Y-direction. If s(i,n) is the flow-compensated MR navigator signal 841 and t(i,n) is the flow-sensitive MR navigator signal 341, the speed of a point $y_n$ along the Y-axis at an instant i is given by:

$$\Delta V(i,n) = arg(FT\{t(i,n)\}) - arg(FT\{s(i,n)\})$$

in which FT is a Fourier transform of the MR navigator signal s(i,n) or t(i,n).

In order to counteract excessive heating of the tissue outside the target region by heat conduction while using one of the methods in accordance with the invention, moreover, the pulse duration of the ultrasound pulses can be limited, for example to a pulse duration of approximately 0.5 s. The duration of the intervals between successive ultrasound pulses can also be adapted. A suitable interval duration is, for example between 30 and 60 seconds.

We claim:

1. A method of irradiating a moving target region within a body by ultrasound comprising:
    performing by a magnetic resonance (MR) device the steps of
        generating and receiving MR signals in the body,
        processing the received MR signals,
        determining automatically movement of the moving target region from the processed MR signals and,
        generating automatically from the determined movement a control signal representing the determined movement of the moving target region,
    performing by an ultrasound device the step of
        irradiating automatically the body with ultrasound, the ultrasound device being responsive to the generated control signal so that a focal region of the ultrasound is in the moving target region, and
    repeating the prior steps in order that the focal region of the ultrasound remains within the moving target region.

2. The method of claim 1 wherein the generated MR signals comprise first navigator signals.

3. The method of claim 2 wherein said step of determining movement comprises detecting an edge in the processed MR navigator signals.

4. The method of claim 2 wherein the first MR navigator signals are flow-sensitive, wherein the MR signals further comprise second flow-compensated MR navigator signals, and wherein said step of determining movement further comprises determining a speed of a moving region in the moving target region from the received first and second MR navigator signals.

5. The method of claim 2 wherein said step of generating the MR navigator signals comprises generating 2D RF pulses for exciting spins in the moving target region, and applying magnetic field gradients to the excited spins.

6. The method of claim 1 wherein the generated control signal represents a position of the moving target region.

7. The method of claim 6 wherein said step of irradiating comprises adjusting automatically the focal region of the ultrasound to a position represented by the generated control signal.

8. The method of claim 1 wherein said step of processing of the received MR signal comprises reconstructing an MR image.

9. The method of claim 8 wherein the MR signals are generated using a fast MR imaging pulse sequence.

10. The method of claim 8 wherein said step of determining movement comprises segmenting a reconstructed MR image.

11. The method of claim 1 wherein the control signal represents when the focal region of the ultrasound is in the moving target region.

12. The method of claim 11 wherein said step of generating a control signal comprises determining automatically a period during which the focal region of the ultrasound is situated within the moving target region, and wherein said step of irradiating comprises generating at least one ultrasound pulse during the period thus determined.

13. The method of claim 1 wherein the generated control signal represents a speed of the moving target region.

14. A device for irradiating a moving target region within a body by ultrasound comprising:
    a magnetic resonance (MR) device comprising receiving means for generating and MR signals from the body,
    means for processing the received MR signals and,
    means for determining automatically movement of the moving target region from the processed MR signals and for generating automatically from the determined movement a control signal representing the determined movement of the moving target region, and
    an ultrasound device for generating ultrasound to which the generated control signal is applied and which is responsive to the generated control signal so that a focal region of ultrasound radiation is in the moving target region.

15. The device of claim 14 wherein said means for determining generates a control signal which represents a position of the moving target region.

16. The device of claim 15 wherein said ultrasound device comprises a position control input, said ultrasound device being responsive to the position control input so that the focal region of generated ultrasound is at the position presented to the position control input, and the generated control signal being applied to the position control input.

17. The device of claim 16 wherein said MR device and said ultrasound device further comprise means for functioning repetitively whereby the focal region of ultrasound is repetitively controlled by repetitively generated control signals.

18. The device of claim 14 wherein said means for determining generates a control signal which represents a trigger reflecting when the focal region of the ultrasound is in the moving target region.

19. The device of claim 18 wherein said ultrasound device comprises a trigger input, said ultrasound device being responsive to the trigger input so that ultrasound radiation is generated upon presentation of a signal to the trigger input, and the generated control signal being applied to the trigger input.

20. The device of claim 14 wherein said means for determining comprises means for execution of an edge detection algorithm.

21. The device of claim 14 wherein said means for determining comprises means for execution of an image segmentation technique.

* * * * *